United States Patent
Vallittu et al.

(10) Patent No.: US 9,144,630 B2
(45) Date of Patent: Sep. 29, 2015

(54) COMPOSITE AND ITS USE

(75) Inventors: Pekka Vallittu, Kuusisto (FI); Kalle Aitasalo, Turku (FI); Matti Peltola, Turku (FI); Lippo Lassila, Lielax (FI); Sari Tuusa, Lemu (FI); Toini Peltola, legal representative, Turku (FI)

(73) Assignee: Skulle Implants Oy, Turku (FI)

( * ) Notice: Subject to any disclaimer, the term of this patent is extended or adjusted under 35 U.S.C. 154(b) by 169 days.

(21) Appl. No.: 13/147,085

(22) PCT Filed: Jan. 29, 2010

(86) PCT No.: PCT/FI2010/050052
§ 371 (c)(1),
(2), (4) Date: Dec. 15, 2011

(87) PCT Pub. No.: WO2010/086508
PCT Pub. Date: Aug. 5, 2010

(65) Prior Publication Data
US 2012/0089237 A1    Apr. 12, 2012

(30) Foreign Application Priority Data

Jan. 30, 2009   (FI) .................................... 20095084

(51) Int. Cl.
*A61L 27/50* (2006.01)
*A61F 2/28* (2006.01)
(Continued)

(52) U.S. Cl.
CPC .............. *A61L 27/50* (2013.01); *A61F 2/2803* (2013.01); *A61F 2/2875* (2013.01); *A61L 27/446* (2013.01); *A61L 27/48* (2013.01); *A61L 27/56* (2013.01); *A61L 31/128* (2013.01); *A61L 31/129* (2013.01); *A61L 31/146* (2013.01); *A61L 31/18* (2013.01); *A61F 2/3094* (2013.01); *A61F 2/30965* (2013.01); *A61F 2002/30011* (2013.01); *A61F 2002/30032* (2013.01); *A61F 2002/3092* (2013.01); *A61F 2002/30971* (2013.01); *A61F 2240/001* (2013.01); *A61F 2250/003* (2013.01); *A61F 2250/0023* (2013.01); *Y10T 428/24942* (2015.01)

(58) Field of Classification Search
CPC ............................. A61F 2/2875; A61F 2/2846
USPC ............................................ 623/17.18, 17.19
See application file for complete search history.

(56) References Cited

U.S. PATENT DOCUMENTS 3,402,055 A    9/1968 Harris et al. .................... 106/50
3,616,319 A *  10/1971 Johnson et al. ............... 205/417
(Continued)

FOREIGN PATENT DOCUMENTS

DE    34 06 689      8/1985
JP    10315362       12/1998
(Continued)

*Primary Examiner* — Bruce E Snow
*Assistant Examiner* — Melissa Hoban
(74) *Attorney, Agent, or Firm* — James C. Lydon

(57) ABSTRACT

The present invention relates to a composite comprising a structural part, a porous part, and at least two interconnecting parts arranged at a distance from each other and extending from the structural part to the porous part, thus connecting them to each other. The implant is characterized in that each interconnecting part is in the form of a band having a length, a width and a height, the width and the height both being independently at most 20% of the length of the band, and in that at least one of the interconnecting parts is at least partially embedded into the structural and porous parts.

13 Claims, 7 Drawing Sheets

(51) Int. Cl.
*A61L 27/44* (2006.01)
*A61L 27/48* (2006.01)
*A61L 27/56* (2006.01)
*A61L 31/12* (2006.01)
*A61L 31/14* (2006.01)
*A61L 31/18* (2006.01)
*A61F 2/30* (2006.01)

(56) References Cited

U.S. PATENT DOCUMENTS

| | | | |
|---|---|---|---|
| 3,674,722 A * | 7/1972 | Rainer et al. | 521/88 |
| 3,828,839 A * | 8/1974 | Dhingra | 164/97 |
| 3,971,670 A * | 7/1976 | Homsy | 156/196 |
| 4,125,581 A * | 11/1978 | Rasmussen | 264/49 |
| 4,392,828 A * | 7/1983 | Ehrnford | 433/217.1 |
| 4,498,941 A * | 2/1985 | Goldsworthy | 156/148 |
| 4,578,826 A * | 4/1986 | Adiletta | 2/167 |
| 4,588,443 A * | 5/1986 | Bache | 106/644 |
| 4,613,784 A * | 9/1986 | Haun et al. | 310/358 |
| 4,716,062 A * | 12/1987 | Klein | 428/515 |
| 4,849,276 A * | 7/1989 | Bendig et al. | 428/117 |
| 4,851,046 A | 7/1989 | Low et al. | 106/35 |
| 4,863,472 A * | 9/1989 | Tormala et al. | 623/23.58 |
| 4,892,786 A * | 1/1990 | Newkirk | 428/307.3 |
| 4,936,939 A * | 6/1990 | Woolum | 156/285 |
| 4,997,656 A * | 3/1991 | Shikinami et al. | 424/448 |
| 5,084,051 A | 1/1992 | Tormala et al. | 606/77 |
| 5,725,577 A | 3/1998 | Saxon | 623/11 |
| 5,824,088 A | 10/1998 | Kirsch | 623/16 |
| 5,846,640 A | 12/1998 | Vallittu | 428/306.6 |
| 5,891,233 A | 4/1999 | Salonen et al. | 106/35 |
| 5,919,234 A | 7/1999 | Lemperle et al. | 623/16 |
| 6,030,220 A | 2/2000 | Karmaker et al. | 433/215 |
| 6,153,221 A | 11/2000 | Thut et al. | 424/484 |
| 6,197,410 B1 | 3/2001 | Vallittu et al. | 428/292.1 |
| 6,270,348 B1 | 8/2001 | Petersen | 433/228.1 |
| 6,280,473 B1 | 8/2001 | Lemperle et al. | 623/16.11 |
| 6,328,765 B1 | 12/2001 | Hardwick et al. | 623/23.72 |
| 6,350,284 B1 | 2/2002 | Tormala et al. | 623/17.19 |
| 6,381,989 B1 | 5/2002 | Karmaker et al. | 65/384 |
| 6,409,764 B1 | 6/2002 | White et al. | 623/16.11 |
| 6,497,729 B1 | 12/2002 | Moussy et al. | 623/23.57 |
| 6,530,956 B1 | 3/2003 | Mansmann | 623/18.11 |
| 6,595,776 B2 | 7/2003 | Kangasniemi et al. | 433/81 |
| 6,599,125 B1 | 7/2003 | Freilich et al. | 433/212.1 |
| 6,641,893 B1 | 11/2003 | Suresh et al. | 428/105 |
| 6,712,851 B1 | 3/2004 | Lemperle et al. | 623/16.11 |
| 6,733,288 B2 | 5/2004 | Vallittu et al. | 433/20 |
| 6,736,854 B2 | 5/2004 | Vadurro et al. | 623/23.72 |
| 6,881,062 B2 | 4/2005 | Kangasniemi et al. | 433/226 |
| 7,001,181 B2 | 2/2006 | Kangasniemi et al. | 433/81 |
| 7,066,962 B2 | 6/2006 | Swords | 623/17.18 |
| 7,186,759 B2 | 3/2007 | Seppala et al. | 523/113 |
| 7,235,290 B2 | 6/2007 | Vallittu et al. | 428/296.7 |
| 7,241,486 B2 | 7/2007 | Pirhonen | 428/297.4 |
| 7,354,969 B2 | 4/2008 | Vallittu et al. | 524/504 |
| 7,435,764 B2 | 10/2008 | Vallittu et al. | 523/117 |
| 7,589,133 B2 | 9/2009 | Pomrink | 523/115 |
| 7,674,477 B1 | 3/2010 | Schmid et al. | 424/422 |
| 7,727,542 B2 | 6/2010 | DiBenedetto et al. | 424/426 |
| 7,731,756 B2 | 6/2010 | Maspero et al. | 623/23.51 |
| 7,879,108 B2 | 2/2011 | Vadurro et al. | 623/23.72 |
| 7,988,733 B2 | 8/2011 | Shimp et al. | 623/17.11 |
| 7,998,375 B2 | 8/2011 | Karmaker et al. | 264/19 |
| 8,007,854 B2 | 8/2011 | Wei et al. | 427/2.1 |
| 8,119,152 B2 | 2/2012 | Shikinami | 424/424 |
| 8,137,103 B1 | 3/2012 | Freilich et al. | 433/172 |
| 8,152,848 B2 | 4/2012 | Freilich et al. | 623/16.11 |
| 8,206,450 B2 | 6/2012 | Henry et al. | 623/17.18 |
| 8,206,457 B2 | 6/2012 | Luginbuehl et al. | 623/23.72 |
| 8,231,685 B2 | 7/2012 | Fritz et al. | 623/23.57 |
| 2003/0003127 A1 | 1/2003 | Brown et al. | 424/423 |
| 2004/0258732 A1 | 12/2004 | Shikinami | 424/426 |
| 2005/0100578 A1 * | 5/2005 | Schmid et al. | 424/423 |
| 2005/0136764 A1 | 6/2005 | Sherman et al. | 442/103 |
| 2006/0116682 A1 | 6/2006 | Longo | 606/69 |
| 2006/0224242 A1 | 10/2006 | Swords et al. | 623/17.19 |
| 2007/0061015 A1 | 3/2007 | Jensen et al. | 623/23.51 |
| 2007/0112434 A1 | 5/2007 | Hakamatsuka et al. | 623/23.5 |
| 2007/0156238 A1 | 7/2007 | Liao et al. | 623/14.12 |
| 2008/0255561 A1 * | 10/2008 | Tormala et al. | 606/77 |
| 2008/0260801 A1 | 10/2008 | Ahlers et al. | 424/426 |
| 2008/0306609 A1 | 12/2008 | Lee et al. | 623/23.58 |
| 2009/0265017 A1 | 10/2009 | McKay | 623/23.63 |
| 2010/0121463 A1 * | 5/2010 | Tormala et al. | 623/23.75 |
| 2010/0168871 A1 | 7/2010 | Liao et al. | 623/23.72 |
| 2011/0038911 A1 | 2/2011 | Sakamoto et al. | 424/423 |
| 2011/0144763 A1 | 6/2011 | Bagga et al. | 623/23.61 |
| 2012/0277743 A1 | 11/2012 | Vallittu | 606/53 |

FOREIGN PATENT DOCUMENTS

| | | |
|---|---|---|
| WO | WO 96/21628 | 7/1996 |
| WO | WO 96/25911 | 8/1996 |
| WO | WO 99/45890 | 9/1999 |
| WO | WO 2004/103319 | 12/2004 |
| WO | WO 2005/048897 | 6/2005 |
| WO | WO 2005/118744 | 12/2005 |

* cited by examiner

COMPOSITE AND ITS USE

The present invention relates to a composite comprising a structural part, a porous part, and at least two interconnecting parts arranged at a distance from each other and extending from the structural part to the porous part, thus connecting them to each other, useful in reconstruction of bones and cartilage as well as in implants. The invention also relates to a method for manufacturing a composite comprising a structural part, a porous part and at least two interconnecting parts.

BACKGROUND OF THE INVENTION

The use of reinforced composites made of particulate fillers or reinforcing fibres has been gaining popularity in dental and medical fields. Several fibre reinforced composites are already known. The state-of-the-art fibre reinforced composites yield high strength properties and by selecting the multiphase resin matrix for the composite, the handling characteristics of the composite can be considerably improved. These have been described, for example, in the patent applications WO 96/25911 and WO 99/45890.

On the other hand, a lot of development has occurred with bioactive materials, namely bioactive ceramics and glass and sol-gel processed silica. These materials can be used to achieve attachment of e.g. bone to a biomaterial surface after the material has been put in contact with tissue. An additional advantage of bioactive glass is its antimicrobial effect on the microbes existing for instance in sinuses of a bone. These properties have been described in several articles and patent applications, such as WO 96/21628 and Zehnder et al., J Endod 2004 April; 30(4):220-4.

From a surgical perspective individual replacement of bone, cartilage and soft tissues are insufficient in tumour, traumatologic and tissue reconstruction surgery despite the increasing advances in biomaterials research and their clinical application methods and tissue engineering. The need and indications for development of new kinds of materials result from disadvantages of the use of allografts. Risks for transmittable diseases (HIV, Creutzfeld-Jacob's disease, etc.) are related to allografting. Metals are not bioactive or osteoconductive, and their use results in stress shielding phenomena and bone atrophy of the adjacent bone. Metal implants cause also severe problems in magnetic resonance imaging (MRI) when diagnosing diseases of patients. These main disadvantages are well documented in large clinical series. On the other hand, medical treatments based on stem cells are becoming an option for treating tissue damages. Stem cell treatment in large reconstruction cases requires use of scaffolds with certain porosity. Currently, the scaffolds are made of biodegradable polymers and non-resorbable porous fibre reinforced composites have not been used for combining regenerative treatment stem cells and reconstructive treatment by fibre composite implants.

Document US 2007/0061015 discloses a biocompatible implement for bone and tissue regeneration having a layered structure. The layered structure can be reinforced by adding strips on the outer surface of the implement. In document US 2004/0258732 an implant material is made by combining a porous article and a pin penetrating through the porous article.

Several different composites comprising bioactive material and imitating bone structure have been presented, for example in applications WO 2004/103319 and WO2005/118744. A problem encountered with these materials is their insufficient mechanical strength. Another problem with these materials is the weak attachment of the porous material (having a low degree of impregnation with the matrix resin) to the load bearing material. A yet further problem is that the particles that are added to the material to enhance the osteoconductivity tend to get loose and disappear from the material before it is placed into the final position.

OBJECTS AND SUMMARY OF THE INVENTION

An object of the present invention is to provide a biologically compatible material that does not have the above-listed drawbacks, or at least those disadvantages are minimised. Specifically, an object of the present invention is to provide a material useful for medical, dental and surgical uses, such as for bone grafting. A further object of the present invention is to provide a material and composite that has good mechanical properties and in which additional particles can be used in a secure manner. It is moreover an object of the present invention to provide an implant structure that can be used as a scaffold for stem cell seeding.

The present invention thus relates to a composite comprising a structural part, a porous part, and at least two interconnecting parts arranged at a distance from each other and extending from the structural part to the porous part, thus connecting them to each other. In a typical composite according to the present invention, each interconnecting part is in the form of a band having a length, a width and a height, the width and the height both being independently at most 20% of the length of the band, and at least one of the interconnecting parts is at least partially embedded into the structural and porous parts.

The invention also relates to the use of these composites in dental and medical applications. The invention still relates to a method for manufacturing a composite comprising a structural part, a porous part and at least two interconnecting parts.

DETAILED DESCRIPTION OF THE INVENTION

Figure 1:
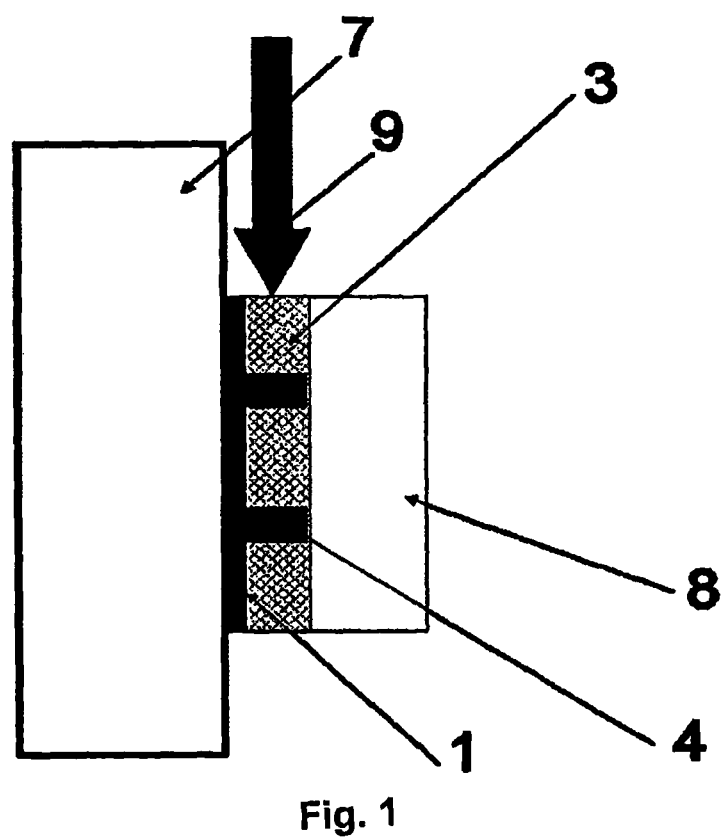
FIG. 1 illustrates testing of a composite according to a first embodiment of the present invention.

The invention is defined in the appended independent claims.

The present invention relates to a composite comprising a structural part, a porous part, and at least two interconnecting parts arranged at a distance from each other and extending from the structural part to the porous part, thus connecting them to each other. In a typical composite according to the present invention, each interconnecting part is in the form of a band having a length, a width and a height, the width and the height both being independently at most 20% of the length of the band, and at least one of the interconnecting parts is at least partially embedded into the structural and porous parts.

The different parts of the composite, structural, porous and interconnecting parts all form integral parts of the composite. The present invention thus fulfils the objects listed above, i.e. it provides a material useful for medical, dental and surgical uses, such as for bone grafting, which material has good mechanical properties, as will be shown in the Experimental part below, and in which additional particles can be used in a secure manner.

The porous part of the composite enhances the growth of new bone, cartilage etc. and the structural part provides the mechanical strength. The interconnecting parts then bind these two parts together and provide the shear strength to the composite, while also increasing the compression and tensile strength of the composite. A further advantage of this invention is that it allows to manufacture implant material that is very much similar to real bone, i.e. to avoid using allografts. On the other hand, traditional metallic implants are less and less desired due to the increase of magnetic resonance imaging. The present invention thus provides for an implant material that is both safe (no risk of contamination as with allografts) and that does interfere with currently used imaging systems (as metal does).

A yet further advantage of the present invention and the use of the interconnecting parts in the form of bands is that the bands give a better reinforcing effect than pins. Moreover, the use of bands allows to use the capillary forces during the healing, thus improving the blood flow into the implant and guiding the cell growth.

The porous part of the composite enables seeding of the embryonic, hematopoietic or mesenchymal stem cells to the implant fastening the attachment of the implant to the bone or cartilage after being inserted to the body. Thus, the material of the present invention allows using stem cells in regenerative medical treatment in combination with non-metallic fibre reinforced composite in reconstructive medical treatment.

In this application, by curing it is meant polymerisation and/or crosslinking. By matrix, it is understood the continuous phase of the composition and by uncured matrix it is meant a matrix that is in its deformable state but that can be cured, i.e. hardened, to an essentially non-deformable state. The uncured matrix may already comprise some long chains but it is essentially not yet polymerized and/or crosslinked. By prepreg, it is meant a semi-manufactured product, that is, a product that is not or only partly polymerized, but yet still deformable. The polymerisation, i.e. curing of a resin leads to a composite material.

The interconnecting parts are in the form of a band, such as a strip, a bar or a cylinder. They can be either straight or curvy, for example they can follow the shape of the blood vessels that will grow within the implant once it is positioned into the patient. According to a preferred embodiment, the interconnecting parts are arranged such that the blood vessels, especially the large vessels, will naturally grow in between them, as blood vessels and bone would typically not grow through the interconnecting parts. Most preferable the outer surface of the implant is not covered with a material similar to that of the interconnecting parts, as that might prohibit the ingrowth of the tissues. Preferably, the outer surface is covered with a layer of a dense material that has been perforated to allow the body fluids to flow within the implant. With time, this layer will degrade.

According to an embodiment of the invention, the width and the height of the interconnecting part are both independently at most 15% of the length of the interconnecting part. The length is thus the largest dimension of the interconnecting part. In practice, the length of the interconnecting part depends on the dimensions of the finished implant.

According to one embodiment of the present invention, said structural part and said porous part both comprise fibres and a matrix. According to yet another embodiment, the amount of fibres per volume of the structural part is larger than the amount of fibres per volume of the porous part. Further, the amount of matrix per volume of the structural part can be larger than the amount of matrix per volume of the porous part.

The structural part thus preferably has a higher density than the porous part, and the degree of impregnation of the fibres by the resin forming the matrix is higher than in the porous part. The impregnation degree of the parts may vary from 5 to 100%.

According to one embodiment, the interconnecting part consists of a matrix material, i.e. of a polymer. According to another embodiment, the interconnecting part further comprises fillers and a matrix. It may thus be either made of filled polymer or it may also comprise reinforcing material, such as fibres, and be thus made of a composite. Preferably there is more than two interconnecting parts which are each at a distance from each other. This distance can be for example 1-100 mm. Suitable distances between the interconnecting parts are from 0.5, 1, 3, 6, 10, 15, 25, 30, 35, 40 or 50 mm up to 3, 5, 10, 14, 15, 20, 30, 40, 55, 65, 80 or 100 mm. The distance between two particular interconnecting parts does not need to be identical to the distance between two other particular interconnecting parts, although the distribution of the interconnecting parts may also be homogenous and regular. The distance of the interconnecting parts from each other is used to simulate the original bones and bone structure and has an important influence on the capillary forces in the implant during healing.

The interconnecting parts extend from the porous part to the structural part, and preferably have the same height (thickness) as the thickness of the composite, i.e. they extend on the whole thickness of the composite. The thickness of the composite can be for example from 0.05 to 5 mm or larger.

According to one preferred embodiment of the invention, the matrix materials of the structural part, the porous part and the interconnecting part consist of same components in differing amounts. This enhances the bonds between the parts, as the chemical structures of the matrixes are identical. An example of this is given in the Experimental part.

When the composite according to the present invention is ready for use, at least a part of at least one matrix may be in partially uncured form in order to allow the composite to be shaped to the required shape. The shaping can also be done before the actual use of the composite, for example on a model reconstructing the defect to be treated.

The fibres may be any suitable fibres known per se, for example selected from the group consisting of glass fibres, silica fibres, carbon/graphite fibres, ceramic fibres, aramid fibres, zylon fibres, polyethylene fibres, polytetrafluoroethylene fibres, such as Teflon® fibres, poly(p-phenylene-2,6-benzobisoxazole) fibres, poly(2,6-diimidazo(4,5-b4',5'-e)pyridinylene-1,4(2,5-dihydro)phenylene fibres, polyolefin fibres, fibres prepared from copolymers of olefins, polyester fibres, polyamide fibres and mixtures thereof. Poly(p-phenylene-2,6-benzobisoxazole) fibres and poly(2,6-diimidazo (4,5-b4',5'-e)pyridinylene-1,4(2,5-dihydro)phenylene fibres belong to a group called rigid-rod polymer fibres. It is obvious to a person skilled in the art that any other known fibres may be used in the present invention, provided that it is possible to obtain a suitable adhesion between said fibres and matrix, in order to achieve the desired mechanical properties. Preferably, glass fibres are used in dental applications. In applications where load-bearing capacity is needed, continuous biostable fibres are preferred.

According to one embodiment of the invention, the fibres are selected from the group consisting of inert glass fibres, bioactive glass fibres, silica fibres, quartz fibres, ceramic fibres, carbon/graphite fibres, aramid fibres, ceramic fibres, poly(p-phenylene-2,6-benzobisoxazole) fibres, poly(2,6-diimidazo(4,5-b4',5'-e)pyridinylene-1,4(2,5-dihydro)phenylene fibres, polyolefin fibres, fibres prepared from copolymers of olefins, polyester fibres, polyamide fibres, polyacrylic fibres, sol-gel processed silica fibres, collagen fibres, cellulose fibres, modified cellulose fibres and mixtures thereof.

The fibres may be in the form of continuous fibres, fibre fabrics, fibre weaves, fibre mats, short fibres and mixtures thereof, and they may be oriented in one direction, two directions, three directions, four directions, randomly or mixtures thereof.

According to one embodiment, the fibres of the structural part are in the form of a woven fabric or a unidirectional fibre roving. The fibres of the porous part are for example in the form of chopped (short), randomly oriented fibres, a woven fabric or a three-dimensional fibre fabric.

The matrix material may comprise monomers selected from the group consisting of methyl acrylate, ethyl acrylate, propyl acrylate, isopropyl acrylate, n-hexyl acrylate, styryl acrylate, allyl acrylate, methyl methacrylate, ethyl methacrylate, propyl methacrylate, isopropyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diurethane dimethacrylate, acetoacetoxy ethyl methacrylate (AAEM), methacrylate functionalized dendrimers, other methacrylated hyperbranched oligomers, hydroxymethyl methacrylate, hydroxymethyl acrylate, hydroxyethyl methacrylate, hydroxyethyl acrylate, hydroxypropyl methacrylate, hydroxypropyl acrylate, tetrahydrofurfuryl methacrylate, tetrahydrofurfuryl acrylate, glycidyl methacrylate, glycidyl acrylate, triethylene glycol diacrylate, tetraethylene glycol dimethacrylate, tetraethylene glycol diacrylate, trimethylolethane trimethacrylate, trimethylolpropane trimethacrylate, pentaerythritol trimethacrylate, trimethylolethane triacrylate, trimethylolpropane triacrylate, pentaerythritol triacrylate, pentaerythritol tetramethacrylate, pentaerythritol tetra-acrylate, ethylene dimethacrylate, ethylene diacrylate, ethylene glycol dimethacrylate, diethylene glycol dimethacrylate, triethylene glycol dimethacrylate (TEGDMA), ethylene glycol diacrylate, diethyleneglycol diacrylate, butylene glycol dimethacrylate, butylene glycol diacrylate, neopentyl glycol dimethacrylate, neopentyl glycol diacrylate, 1,3-butanediol dimethacrylate, 1,3-butanediol diacrylate, 1,4-butanediol dimethacrylate, 1,4-butanediol diacrylate, 1,6-hexanediol dimethacrylate, 1,6-hexanediol diacrylate, di-2-methacryloxyethyl-hexamethylene dicarbamate, di-2-methacryloxyethyl-trimethylhexamethylene dicarbamate, di-2-methacryloxyethyl-dimethylbenzene dicarbamate, di-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2-bis(4-(2-hydroxy-3-methacryloxy)phenyl)propane (BisGMA), 2,2'-bis(4-methacryloxyphenyl)propane, 2,2'-bis(4-acryloxyphenyl)propane, 2,2'-bis[4(2-hydroxy-3-acryloxyphenyl)propane, 2,2'-bis(4-methacryloxyethoxyphenyl)propane, 2,2'-bis(4-acryloxyethoxyphenyl)-propane, 2,2'-bis(4-methacryloxypropoxyphenyl)propane, 2,2'-bis(4-acryloxy-propoxyphenyl)propane, 2,2'-bis(4-methacryloxydiethoxyphenyl)-propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane and mixtures thereof.

The matrix may also be made of crosslinkable monomers or polymers such as $\epsilon$-caprolactone, polycaprolactone, polylactides, polyhydroxyproline, and other biopolymers as well as polyamides, polyurethane, polyethylene, polypropylene, other polyolefins, polyvinyl chloride, polyester, polyether, polyethyleneglycol, polysaccharide, polyacrylonitrile, poly (methyl methacrylate), phenol-formaldehyde, melamine-formaldehyde, and urea-formaldehyde. The matrix may naturally also consist of a mixture of a monomer(s) and a polymer(s).

Dendrimers having 5 to 35 functional groups (or more) such as methacrylate or acrylate groups, may also be used. Multifunctionality forms highly cross-linked matrix and decreases the creep of the polymer in the long-term use. The functionality of the dendrimers can be changed to be suitable for attaching drug molecules to the denrimer based polymer for allowing local slow drug release from the dendrimer based implant. Examples of suitable dendrimers are given for example in U.S. Pat. No. 5,834,118 (incorporated herein by reference). Dendrimers may particularly be starburst or hyperbranched methacrylated polyesters.

According to one embodiment of the present invention, the matrix can be made of monomer systems of mono-, bi-, or multifunctional acrylates, epoxies, dendrimers, hyperbranched reactive polymers, their combinations, or the like. The matrix may, for example, be selected from the group consisting of mono-, di- and multifunctional acrylates, mono-, di- and multifunctional methacrylates, epoxies, starburst methacrylated polyesters, hyperbranched methacrylated polyesters and mixtures thereof. Optionally, polymers of polymethyl methacrylate, polyvinyl chloride, polyetherketone, polylactides, epsiloncaprolactone or their combinations, or the like may be used. Combinations of monomers and polymers are also suitable to be used.

In dental applications, it is preferred, for the moment, to use dimethacrylates in combination with polymethyl methacrylate as a matrix, because it forms a gel-like matrix before polymerisation. The matrix can be dense or contain pores and holes in the structure depending up to clinical needs. The optimal pore size for endosseus applications is 100 to 500 micrometers when bone ingrowth is considered, but the composite can optionally contain also holes up to 5 millimeters in diameter.

According to an embodiment of the invention, the matrix material is selected from the group consisting of triethylene glycol dimethacrylate, 2,2-bis(4-(2-hydroxy-3-methacryloxy)phenyl)propane, polymethyl methacrylate, methyl methacrylate, hydroxyethyl methacrylate, urethan dimethacrylate, starburst methacrylated polyesters, hyperbranched methacrylated polyesters, polyvinyl chloride, polyetherketone, polylactides, $\epsilon$-caprolactone, poly-OH-proline and mixtures thereof.

The composite according to the invention may further comprise modifier particles. These modifier particles may for example be bioactive and for example improve the osteoconductivity of the composite. The particles may be in the form of particulate fillers or fibres. The weight fraction of these modifier particles in the composite can be for example 10-60 wt-%, such as from 5, 10, 15, 20, 35 or 50 wt-% up to 10, 15, 20, 35, 50, 55, 60 or 75 wt-%.

According to one embodiment, the modifier particles are selected from the group consisting of bioactive ceramics, bioactive glass, silica gel, titanium gel, silica xerogel, silica aerogel, natrium silica glass, titanium gels, bioactive glass ionomer, hydroxyapatite, Ca/P-doped silica gel and mixtures thereof. Any combination of said materials may naturally also be used. When rapid mineralization is needed, it is preferred to have bioactive glass with sol-gel processed silica particles on the porous part of the composite.

The composite according to the present invention may further comprise particulate filler material, such as inert glass, bioactive glass, metal oxides, ceramics, polymers and mixtures thereof. Metal oxides may for example be used as radio or X-ray opaque materials or as colouring materials. It is for example possible to make the composite such that it is not further necessary to coat it with another material to make the final outer surface of the finished device.

The composite may also comprise therapeutically active agents or cells, such as stem cells. Several kind of cells including hematopoietic bone marrow cells, fibroblasts, osteoblasts, regenerative cells, stem cells, like embryonic stem cells, mesenchymal stem cells or adipose stem cells can be seeded to the composite. The embryonic stem cells may or may not be of a human origin. Stem cells seeded to the composite can be cultured in bioreactors ex vivo, in other parts of the body before inserting the formed tissue into its final place, or directly at the place where regenerative and reconstructive treatment is needed. The composite may contain also additives enhancing its processability, such as polymerisation initiators. The materials of the composite can be either bioresorpable, biodegradable, biostable or a mixture of these.

The bending strength of the composite may vary for example from 5 to 500 MPa due to the dense part of the composite. The strength is thus remarkably higher than for known biomaterials having a porous part.

The invention further relates to a use of a composite according to the present invention in dental and medical applications. Said use is for example for replacement of bones or support of the bone fractures. The specific embodiments and details listed above in connection with the composite also apply for the use according to the present invention.

The composite according to the present invention may also comprise other parts required for its further use, as explained below.

According to an embodiment of the invention, the composite further comprises dental implants or studs for dental implants arranged on the structural part at the placement of the interconnecting parts. This has the advantage that when reconstructing a jaw bone, teeth can be positioned to where they are required, and not only to where original bone remains. With the prior art materials, typically the material does not have sufficient strength to withstand biting forces. The dental implants may be manufactured for example from titanium, ceramic materials or a polymeric composite.

The composite according to the present invention may also be used for manufacturing implants for auditory ossicles or veins, for example. Some applications for the composite in contact of soft tissues are stents, catheters and prostheses to assure patency of contracted lumens. The invention thus also relates to a prefabricated stent consisting essentially of a material according to the present invention. Such a prefabricated stent may be used for example in blood vessels, guts, esophagus, gastrointestinal tract, lymph vessels, urinary tract, respiratory tract and nervous system.

The material according to the present invention may thus be used to manufacture any kind of device, and the manufacturing process is evident for a person skilled in the art. The size of the device may vary from micrometer range (such as for auditory ossicle implants) to large pieces of tissue. The material according to the present invention may thus be used for manufacturing "spare parts" such as ears, noses and eyes.

Furthermore, the present materials may be used for manufacturing of nose or facial soft tissues, knee or shoulder prosthesis. Some examples of applications are the use as a load bearing structural biomaterial, for replacement and repair of tissue, bones and skeleton, for retaining soft and cartilage tissues in desired form or for cell and tissue engineering and testing. The composite as structural biomaterial can also be used in long bone replacement, individually formed root canal posts of teeth, dental implants, replacement of vertebra, pelvis, and reconstruction of other skeletal parts such as in repair and replacement of auditory ossicles. The composite can also be used as replacing material for e.g. tumour-invaded tissues. In plastic surgery, the composite can be used to retain soft or cartilage tissue in the position where they give the optimal and desired support for the tissues with regard to the aesthetics and cosmetics of a human body. The composite according to the present invention may be used in both humans and animals.

When different further parts are attached to the composite according to the invention, thus forming an implant, the attachment is preferably done on the placement of the interconnecting parts. The attachment can be performed by mechanical bonding, with adhesives, such as silanes, or by polymerisation (for example by interpenetrating polymer network, IPN).

The present invention thus also relates to an implant comprising a composite according to the present invention. The implant may further comprise stem cells, therapeutically active agents etc.

The invention still relates to a method for manufacturing a composite comprising a structural part, a porous part and at least two interconnecting parts. In this method, the following steps are performed:
 a) a structural part is manufactured and shaped to the final shape required for the composite, and at least partially cured,
 b) the interconnecting parts are formed and positioned on the structural part, at a distance from each other, c) a porous part is manufactured, shaped to correspond to the shape of the structural part and at least partially cured and d) the porous part is pressed on the structural part on the same side as the interconnecting parts.

The method may further comprise a step e) in between the steps b) and d) (i.e. either between the steps b) and c) or between the steps c) and d)) in which modifier particles are arranged on the structural part, between the interconnecting parts.

The method may yet further comprise a step f) of final curing.

The interconnecting parts may be formed, in step b), either as unidirectional composite material that is already in the form of a band, or for example by injecting a paste comprising the components of the interconnecting parts.

The material can thus be used in the manufacturing of the implant on rapid prototyping models to the customised form of the patient's anatomic needs, or the implant can be fabricated to the standardised form to be used in average treatment cases.

In customised and standard composite implant manufacturing, the prepreg of the structural part is formed and polymerized initially by autopolymerisation, light polymerisation, thermal polymerisation, ultrasound or microwave polymerisation on the rapid prototyping model of the reconstruction area. Interconnecting elements in non-polymerised paste form are placed on the surface of the structural part which is desired to be covered with the porous composite, i.e. to be filled with tissue as time passes. The prepreg of the porous material is placed on the interconnecting elements and pressed against the structural part. Particles of bioactive glass or the like are powdered on the structural part before placing the porous prepreg on it. Interconnective elements and porous composite prepreg are polymerized simultaneously by autopolymerisation, light polymerisation, thermal polymerisation, ultrasound or microwave polymerisation. The composite is post-polymerised at a temperature allowing an optimal degree of monomer conversion, i.e. at a temperature close to the glass transition temperature of the polymer matrix. The composite implant is thereafter preferably packed and sterilized by heat, steam, hydrogen peroxide, supercritical carbon dioxide or by radiation. A typical shelf-life for these products is about one year.

The specific embodiments and details listed above in connection with the composite and use also apply for the implant and method according to the present invention.

DETAILED DESCRIPTION OF THE DRAWINGS

FIG. 1 illustrates testing of a composite according to a first embodiment of the present invention. This testing is explained in more detail in the Experimental part.

Figure 2:
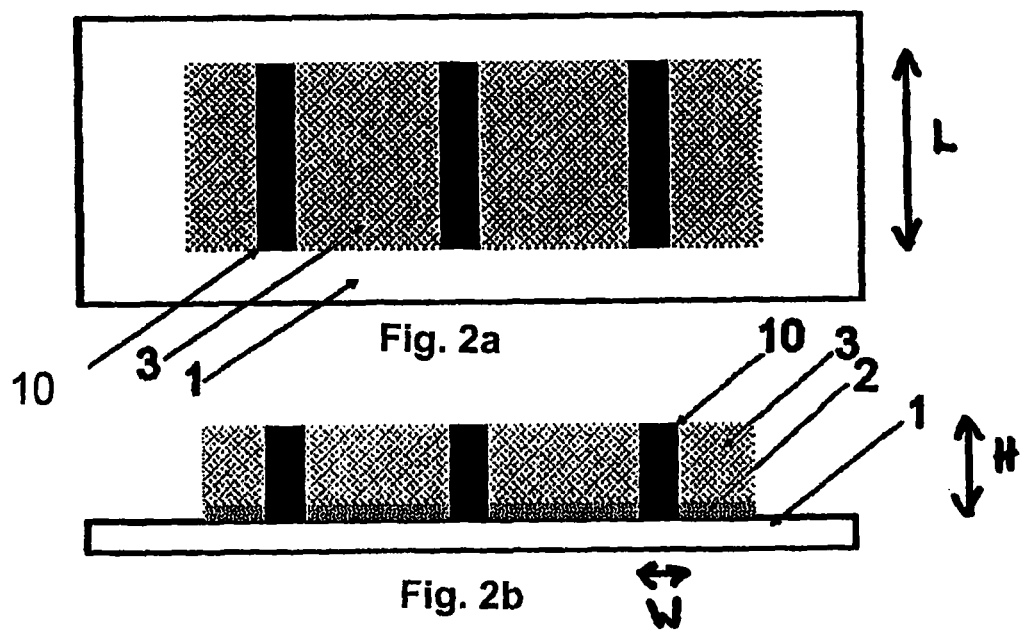
FIGS. 2a and 2b illustrate a composite according to a second embodiment of the invention.

FIGS. 2a and 2b illustrate a composite according to a second embodiment of the invention. In this embodiment, the structural part 1, bioactive particles 2 and porous layer 3 are interconnected with longitudinal, rectangular bands 10 as can be seen in FIG. 2a viewed from above. The length L, height H and width W of the bands 10 are also shown in these Figures.

Figure 3:
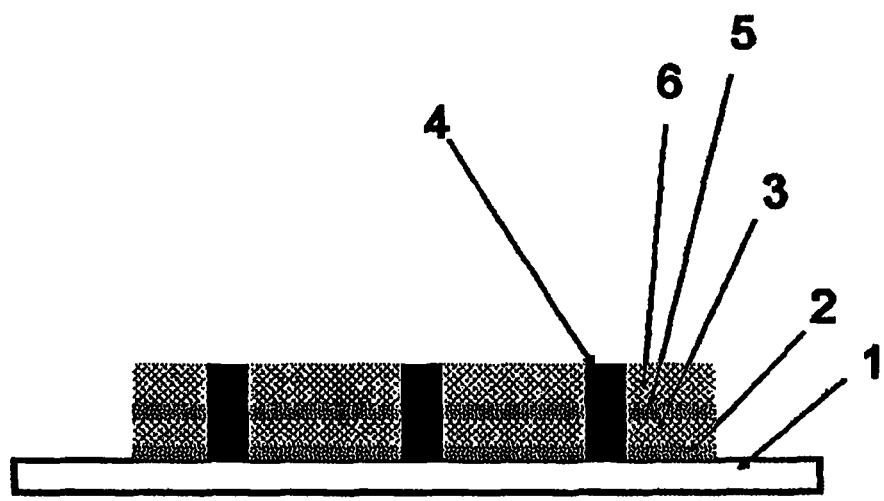
FIG. 3 illustrates a composite according to a third embodiment of the invention.

FIG. 3 illustrates a composite according to a third embodiment of the invention. In this embodiment, two porous parts 3 and 6 are arranged on the structural part 1. Bioactive particles 2 and 5 are arranged on the two interfaces and all these parts are interconnected with interconnecting parts 4 in the form of bands.

Figure 4:
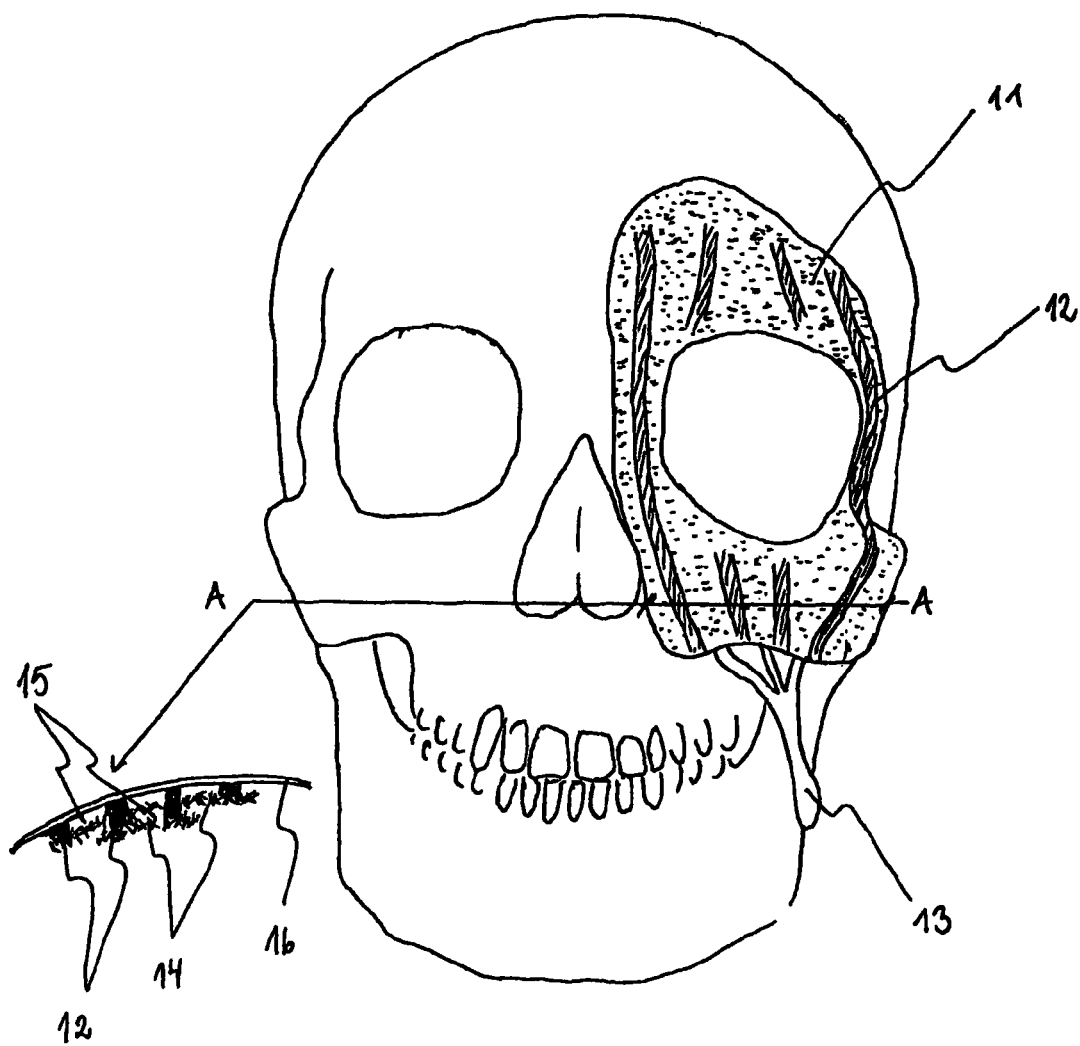
FIG. 4 illustrates an implant and its use according to a fourth embodiment of the invention.

FIG. 4 illustrates an implant and its use according to a fourth embodiment of the invention. The Figure shows a facial view of a maxillofacial implant 11 containing continuous interconnecting bands 12 along the direction of the facial blood vessel arteries 13. A cross-sectional view along the line A-A shows the structure of the implant, i.e. the interconnecting bands 12 that are embedded in the porous layers 14 of the implant, thus connecting them to each other and holding them together. The porous layers also provide for spaces 15 for bioactive particles (not shown for sake of clarity) as well as for bone and arterial ingrowth. The surface of the implant consists of a surface layer 16.

Figure 5:
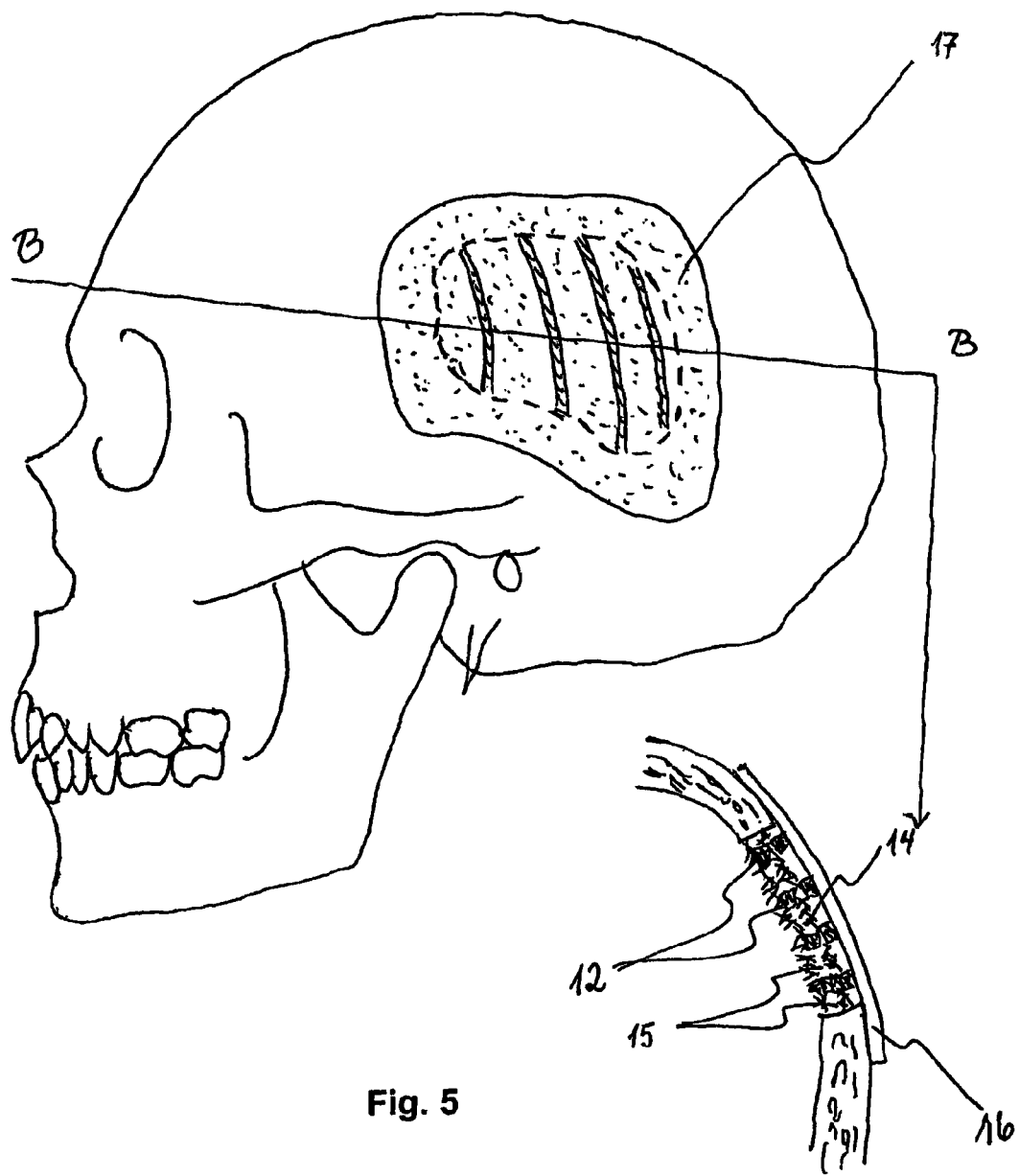
FIG. 5 illustrates an implant and its use according to a fifth embodiment of the invention.

FIG. 5 illustrates an implant and its use according to a fifth embodiment of the invention. The Figure shows a sagittal view of a cranioplasty implant 17 replacing a part of the bone os parietalis after a brain operation. A cross-sectional view along the line B-B shows the structure of the implant, i.e. the interconnecting bands 12, the spaces 15 for bone ingrowth and the porous layers 14. The implant also comprises an outer surface layer 16.

Figure 6:
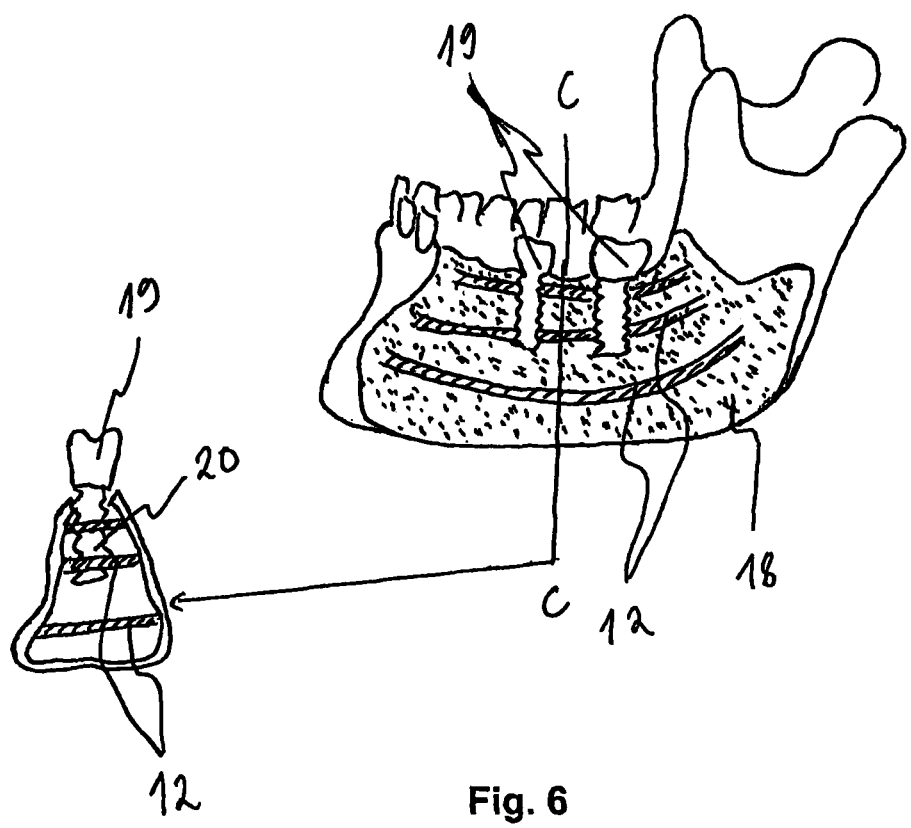
FIG. 6 illustrates an implant and its use according to a sixth embodiment of the invention.
Figure 7:
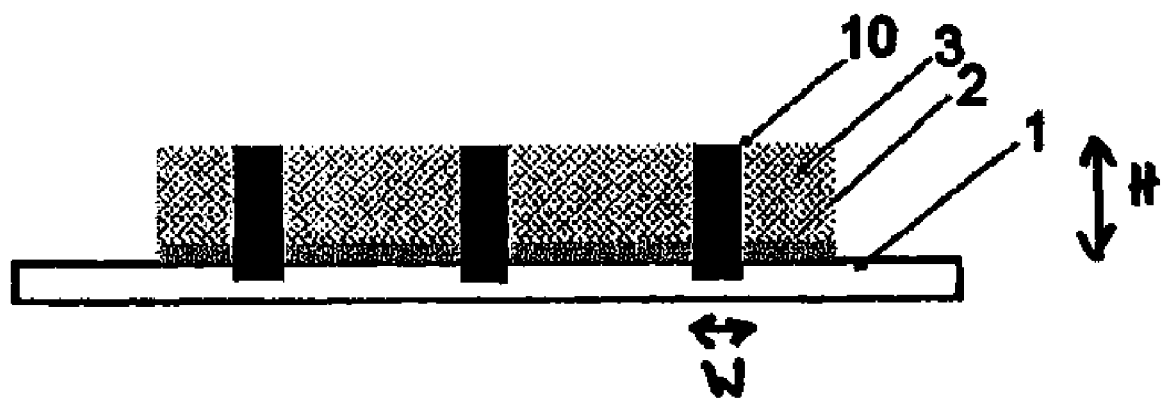
FIG. 7 shows the composite of FIG. 2b, but additionally illustrates rectangular band 10 partially embedded in structural part 1.

FIG. 6 illustrates an implant and its use according to a sixth embodiment of the invention. The Figure shows a lower jaw bone (os mandibularis) having a reconstructive implant 18 with dental implants 19 anchored to the interconnecting bands 12 of the implant. A cross-sectional view along the line C-C shows how the root 20 of a dental implant 19 is anchored to the interconnecting bands 12, in order to withstand the shear forces applied to dental implants by chewing.

EXPERIMENTAL PART

Some composites according to the present invention were manufactured and their strength tested as explained below.

Example 1

A bilayered composite was manufactured using woven E-glass fibre fabric (120 g/m$^2$) that was impregnated with a monomer resin mixture of bisGMA-TEGDMA (70:30 wt-%) including a photosensitive initiator-activator system. The resin impregnated fabric was used in four layers to obtain a dense load-bearing laminate for the composite. The glass fibre-resin ratio was 65 wt-% to 35 wt-%. The final thickness of the structural part, the dense laminate with four layers of woven fabric was 1 mm. The laminate was photopolymerised to the shape of the outer surface of the composite.

The porous part of the composite was made of E-glass fibre wool with randomly oriented fibres. The fibre wool was impregnated with a monomer resin mixture of bisGMA-TEGDMA (40:60 wt-%) including a photosensitive initiator-activator system. The low degree of resin impregnation of the wool resulted in interconnective porosities in the part. Glass fibre-resin ratio of the porous part of the composite was 76 wt-% to 24 wt-%. Thickness of the porous part was 3 mm.

The structural part was combined to the porous part by interconnecting bands which were made of a composite resin comprising bisGMA-TEGDMA (40:60 wt-%) including a photosensitive initiator-activator system and silica particulate fillers having an average diameter of 1 μm and a weight ratio of 65% to the weight of the resin. This composite resin is in the paste form and has a viscosity of a typical paste. The paste was sprued to the structural part in order to obtain interconnecting bands of 10 mm in length, 2 mm in width and 1 mm in height. The distance between the interconnecting bands was 10 mm.

A bioactive modifier consisting of granules of bioactive glass was powdered on the surface of the structural part onto the spaces between the interconnecting bands. The granule size of the bioactive glass varied between 0.5 to 0.8 mm. The porous part was placed on the structural part and on the interconnecting bands. The bioactive glass granules were left between the layers. The porous part was pressed against the structural part structural part in order to get penetration of the interconnecting bands through the porous layer. The pressing process spread the interconnecting bands so that the above-mentioned final dimensions were obtained. The interconnecting bands and the porous layer part was then photopolymerised in order to attach it to the structural part. The total weight fraction of bioactive glass in the composite was 26%.

Example 2

A bilayered composite as prepared in Example 1 both with and without the interconnecting bands between the structural part and porous part were tested to demonstrate the influence of the interconnecting bands on shear force resistance of the composite. The structural part was glued to an acrylic block from the outer surface of the composite. The other surface had the porous part attached to the structural part by photopolymerisation of the resin matrix of the porous part only, or by using the interconnecting bands described in the Example 1. Test set-up is shown in FIG. 1.

In FIG. 1, reference number 1 shows the structural part, 7 the acrylic block, 3 the porous part, 4 an interconnecting bands, 8 dental plaster (i.e. plaster of Paris) and 9 denotes the direction of the shear force.

The porous part was filled with plaster of Paris to simulate the situation where bone has grown into the interconnective porosites. After setting of the plaster of Paris, shear force was applied to the porous part and plaster of Paris. Force required to loosen the porous part from the structural part was used as an indicating unit for the shear force resistance of the bilayered composite.

The shear strength showed to be 431 N loading force for specimens without interconnecting bands and 879 N for the specimens with interconnecting bands. The values demonstrate that the interconnecting bands are stressed by shear and that the porous part is attached strongly to the structural part, i.e. the dense laminate by the interconnecting bands.

In this specification, except where the context requires otherwise, the words "comprise", "comprises" and "comprising" mean "include", "includes" and "including", respectively. That is, when, the invention is described or defined as comprising specified features, various embodiments of the same invention may also include additional features. Moreover, the reference signs are not to be construed as limiting the claims.

The invention claimed is:

1. A composite comprising
   a structural part,
   a porous part,
   wherein said structural part and said porous part both comprise fibres and a matrix, such that an amount of fibres per volume of the structural part is larger than an amount of fibres per volume of the porous part, and
   at least two reinforcing parts arranged at a distance from each other, said at least two reinforcing parts separate from and unconnected to one another, said at least two reinforcing parts extending from the structural part to the porous part, thus connecting said structural part to said porous part,
   wherein
   each reinforcing part is in the form of a band having a length, a width and a height, the width and the height both being independently at most 20% of the length of the band,
   at least one of the reinforcing parts is partially embedded into the structural and porous parts, and
   wherein the reinforcing parts each comprise a polymeric matrix.

2. A composite according to claim 1, wherein the width and the height of each reinforcing part is at most 15% of its length.

3. A composite according to claim 1, wherein the fibres of the structural part are in the form of a woven fabric or a unidirectional fibre roving.

4. A composite according to claim 1, wherein the fibres of the porous part are in the form that is selected from the group consisting of chopped, randomly oriented fibres, woven fabric and a three-dimensional fibre fabric.

5. A composite according to claim 1, wherein the reinforcing parts further comprise fillers.

6. A composite according to claim 1, further comprising modifier particles.

7. A composite according to claim 6, wherein the modifier particles improve the osteoconductivity of the composite.

8. A composite according to claim 6, wherein the modifier particles are selected from the group consisting of bioactive ceramics, bioactive glass, silica gel, titanium gel, silica xerogel, silica aerogel, natrium silica glass, titanium gels, bioactive glass ionomer, hydroxyapatite, Ca/P-doped silica gel and mixtures thereof.

9. A composite according to claim 1, wherein the structural part, the porous part and the reinforcing parts each comprise a matrix material, and wherein the matrix materials of the structural part, the porous part and the reinforcing parts consist of same components in different amounts.

10. A composite according to claim 1, further comprising finished dental implants arranged on the reinforcing parts.

11. A composite comprising
    a structural part,
    a porous part,
    wherein said structural part and said porous part both comprise fibres and a matrix, such that an amount of matrix per volume of the structural part is larger than an amount of matrix per volume of the porous part, and
    at least two reinforcing parts arranged at a distance from each other, said at least two reinforcing parts separate from and unconnected to one another, said at least two reinforcing parts extending from the structural part to the porous part, thus connecting said structural part to said porous part,
    wherein
    each reinforcing part is in the form of a band having a length, a width and a height, the width and the height both being independently at most 20% of the length of the band,
    at least one of the reinforcing parts is partially embedded into the structural and porous parts, and
    wherein the reinforcing parts each comprise a polymeric matrix.

12. An implant comprising a composite according to claim 1.

13. An implant according to claim 12, further comprising stem cells.

* * * * *